United States Patent
Putzig et al.

[11] Patent Number: 6,075,115
[45] Date of Patent: Jun. 13, 2000

[54] PROCESS FOR THE PRODUCTION OF 5-SULFO ISOPHTHALATE BIS-GLYCOLATE ESTER METAL SALTS AND OXYSULFONATED POLYESTERS MADE THEREFROM

[75] Inventors: Donald Edward Putzig, Newark; William G Peet, Wilmington, both of Del.

[73] Assignee: E. I. du Pont de Nemours and Company, Wilmington, Del.

[21] Appl. No.: 09/419,762

[22] Filed: Oct. 19, 1999

[51] Int. Cl.[7] ............................. C08G 63/78; C08J 3/02
[52] U.S. Cl. .................. 528/279; 528/274; 528/283; 528/286; 528/294; 524/706; 524/709; 524/710; 524/730; 524/745; 524/765; 524/773
[58] Field of Search ..................... 528/274, 279, 528/283, 286, 294; 524/706, 709, 710, 730, 745, 765, 773

[56] References Cited

U.S. PATENT DOCUMENTS

| | | | |
|---|---|---|---|
| 3,056,818 | 10/1962 | Werber | 260/410.6 |
| 3,326,965 | 6/1967 | Seheitheis et al. | 260/475 |
| 3,338,935 | 8/1967 | Kerschner et al. | 260/429.5 |
| 3,441,540 | 4/1969 | Müller et al. | 260/75 |
| 4,010,145 | 3/1977 | Russin et al. | 260/75 R |
| 4,277,415 | 7/1981 | Sugerman et al. | 260/429.5 |
| 4,361,694 | 11/1982 | Weinberg et al. | 528/279 |
| 4,424,140 | 1/1984 | Weinberg et al. | 502/155 |
| 4,482,700 | 11/1984 | Kühnrich et al. | 528/279 |
| 4,512,928 | 4/1985 | Sugerman et al. | 260/410.9 R |
| 5,015,759 | 5/1991 | Lowe | 560/91 |
| 5,120,822 | 6/1992 | Hoeschele et al. | 528/272 |
| 5,453,479 | 9/1995 | Borman et al. | 528/279 |
| 5,922,828 | 7/1999 | Schiraldi | 528/279 |

FOREIGN PATENT DOCUMENTS

| | | |
|---|---|---|
| 0 634 435 A1 | 1/1995 | European Pat. Off. . |
| 0 812 818 A1 | 12/1997 | European Pat. Off. . |
| 46-27552 | 8/1971 | Japan . |
| 47-26437 | 7/1972 | Japan . |
| 61-11248 | 4/1986 | Japan . |
| 61-25738 | 6/1986 | Japan . |
| 63-15937 | 4/1988 | Japan . |
| 7-39481 | 5/1995 | Japan . |
| WO 97/47675 | 12/1997 | WIPO . |
| WO 99/28033 | 6/1999 | WIPO . |

*Primary Examiner*—Samuel A. Acquah

[57] ABSTRACT

The invention provides a process that can be used for producing a bis-glycolate ester of 5-sulfo isophthalate metal salt. The process comprises contacting a 5-sulfo isophthalate a metal salt or a dialkyl ester of 5-sulfo isophthalate metal salt, in the presence of a catalyst, with a glycol. The catalyst comprises (1) a titanium compound, a solubility promoter, a phosphorus source, and optionally a solvent, (2) a titanium compound, a complexing agent, a phosphorus source, and optionally a solvent, a sulfonic acid, or combinations thereof, or (3) combinations of (1) and (2). The solubility promoter can be selected from the group consisting of ortho silicates, ortho zirconates and combinations thereof. The phosphorus source is selected from the group consisting of a phosphonic acid, a phosphinic acid, a phosphine, and combinations of two or more thereof. The complexing agent can be selected from the group consisting of hydroxycarboxylic acids, aminocarboxylic acids, and combinations thereof. The invention also provides a process that can be used for producing a cationic dyeable polyalkylene terephthalate. The process comprises contacting a mixture, in the presence of an esterification or transesterification catalyst, with a glycol in which the mixture comprises the bis-glycolate ester of 5-sulfo isophthalate metal salt produced by the process disclosed above and either a terephthalate acid or a dialkyl terephthalate.

21 Claims, No Drawings

PROCESS FOR THE PRODUCTION OF 5-SULFO ISOPHTHALATE BIS-GLYCOLATE ESTER METAL SALTS AND OXYSULFONATED POLYESTERS MADE THEREFROM

FIELD OF THE INVENTION

This invention relates to a process for producing bis-glycolate esters of 5-sulfo isophthalate metal salts by esterification of 5-sulfo isophthalic acid metal salts or transesterification of dialkyl ester of 5-sulfo isophthalate metal salts.

BACKGROUND OF THE INVENTION

Polyesters of benzene dicarboxylates and glycols are widely used in thermoplastic fibers, films and molding applications because of their excellent physical properties and surface appearance. Polyethylene terephthalate (PET), polypropylene terephthalate (PPT) and polybutylene terephthalate (PBT) are the more common commercial polyesters within this class of polymers, generally referred to as "polyalkylene terephthalates".

Polyalkylene terephthalates commonly are prepared by one of two routes: (1) transesterification of a dialkyl terephthalate diester (e.g., dimethyl terephthalate DMT) with a diol (e.g., ethylene glycol) to form an intermediate (e.g., bis-hydroxyethyl terephthalate BHT), followed by polycondensation to form the polyalkylene terephthalate (e.g., PET); or (2) by direct esterification of terephthalic acid (TPA) with a glycol (e.g., ethylene glycol), to produce the same BHT intermediate followed by polycondensation to form the polyalkylene terephthalate (e.g., PET). The term "(trans) esterification" is used in this document to refer either to esterification, transesterification, or both.

Cationic dyeable polyesters (CDPET) are produced by using small amounts of sulfonated isophthalate metal salts or their bis-glycolate esters as co-monomers along with DMT or TPA. Fiber made from CDPET copolymer gives brilliant shades on dyeing with basic/cationic dyes and also dyes with disperse dyes to deeper shades and at lower temperatures than fibers made from PET. Typically these cationic dyeable polyesters are made by incorporating up to about 3% of 5-sulfo isophthalic acid (SIPA) or its dimethyl or bis-glycolate ester, generally as the sodium salt. The use of the bis-glycolate ester of 5-sulfo isophthalate sodium salt is particularly preferred because of greater manufacturing efficiency, i.e., shorter polycondensation time for making the sulfo-modified polyalkylene terephthalate.

Catalysts are used to speed the above (trans)esterification and polycondensation reactions. The same or different catalyst may be used for both steps. Many current commercial processes use manganese or zinc salts as the catalyst for the (trans)esterification step. Antimony, in the form of a glycol solution of antimony oxide, is used as the polycondensation catalyst. Organic titanates such as tetraisopropyl titanate and tetrabutyl titanate are also known to be effective (trans) esterification and polycondensation catalysts for preparing polyalkylene terephthalates.

For incorporating sulfo-modified monomers in the above compositions, a bis-glycolate ester of 5-sulfo isophthalate sodium salt can be used. It can be prepared by esterification of 5-sulfo isophthalate sodium salt (NaSIPA), or by transesterification of the dialkyl ester of 5-sulfo-isophthalate sodium salt such as, for example, dimethyl ester of 5-sulfo-isophthalate sodium salt (NaDMSIP). Either tetraisopropyl titanate (see JP 2-117,959) or manganese acetate (see JP 49-117,446 and U.S. Pat. No. 3,899,470) are typically used as (trans)esterification catalyst to enable complete conversion to the bis-glycolate ester. However, these catalysts have a tendency to impart an undesirable yellow tinge to the resulting cationic dyeable polyalkylene terephthalate. There is a need for an improved catalyst for the process of manufacturing the above bis-glycolate ester by (trans) esterification of 5-sulfo isophthalic acid or ester metal salts.

SUMMARY OF THE INVENTION

The first embodiment of the invention relates to a process that can be used for producing a bis-glycolate ester of 5-sulfo isophthalate metal salt. The process comprises contacting the free acid or ester of a 5-sulfo isophthalate metal salt, in the presence of a catalyst, with a glycol.

The catalyst comprises a titanium compound, a solubility promoter, a phosphorus source, and optionally a solvent. The solubility promoter can be selected from the group consisting of ortho silicates, ortho zirconates and combinations thereof. The phosphorus source is selected from the group consisting of a phosphonic acid, a phosphinic acid, a phosphine, and combinations of two or more thereof.

The catalyst can also comprise a titanium compound, a complexing agent, a phosphorus source, and optionally a solvent, a sulfonic acid, or combinations thereof. The complexing agent can be selected from the group consisting of hydroxycarboxylic acids, aminocarboxylic acids, and combinations thereof. The phosphorus source is the same as disclosed above.

The second embodiment of the present invention relates to a process that can be used for producing a cationic dyeable polyalkylene terephthalate. The process comprises contacting a mixture comprising (i) terephthalic acid or dialkyl terephthalate and (ii) the bis-glycolate ester of 5-sulfoisophthalate metal salts produced in the first embodiment of the invention, in the presence of an esterification or transesterification catalyst, with a glycol.

DETAILED DESCRIPTION OF THE INVENTION

According to the first embodiment of the present invention, a process that can be used for producing bis-glycolate esters of 5-sulfo isophthalate metal salts is provided. The starting materials, 5-sulfo isophthalate metal salts or their esters have the formula of $(RO(O)C)_2ArS(O)_2OM$ in which each R can be the same or different and is hydrogen or an alkyl group containing 1 to about 6 carbon atoms. Ar is a phenylene group. M can be an alkali metal ion.

The catalyst composition of this invention is substantially soluble in a solvent. The term "substantially" means more than trivial. It is preferred that the composition be completely soluble in the solvent. However, a substantial portion of the composition can also be suspended or dispersed in the solvent.

The catalyst composition can comprise, consist essentially of, or consist of an organic titanium compound, a solubility promoter, and a phosphorus source. The composition can also consist essentially or consist of an organic titanium compound, a solubility promoter, a phosphorus source, and a solvent. The solubility promoter can be selected from the group consisting of ortho silicates, ortho zirconates, and combinations thereof.

According to the present invention, the preferred titanium compounds are organic titanium compounds. Titanium tetrahydrocarbyloxides are presently the most preferred organic titanium compounds because they are readily available and effective. Examples of suitable titanium tetrahydrocarbyloxide compounds include those expressed by the general formula $Ti(OR')_4$ where each R' is independently selected from the group consisting of an alkyl radical, a cycloalkyl radical, an aralkyl hydrocarbon radical, and combinations of two or more thereof. Each radical can contain from 1 to about 30, preferably 2 to about 18, and most preferably 2 to 12 carbon atoms per radical and each R' can be the same or different. Titanium tetrahydrocarbyloxides in which the hydrocarbyl group contains from 2 to about 12 carbon atoms per radical which is a linear or branched alkyl radical are most preferred because they are relatively inexpensive, more readily available, and effective in forming the solution. Suitable titanium tetrahydrocarbyloxides include, but are not limited to, titanium tetraethoxide, titanium tetrapropoxide, titanium tetraisopropoxide, titanium tetra-n-butoxide, titanium tetrahexoxide, titanium tetra 2-ethylhexoxide, titanium tetraoctoxide, and combinations of any two or more thereof.

The presence of a halide, or of other active substituent, in the R' group generally is avoided since such substituents can interfere with catalytic reactions or form undesired by-products, which can contaminate the polymer when the titanium compound is used for producing a polymer. Presently it is also preferred that the each R' group is identical to facilitate synthesis of the organic titanate. In some cases two or more R' groups can be from a common compound chemically bonded together other than at the titanium atom (i.e., multidentate ligands such as triethanolamine, citric acid, lactic acid, malic acid, tartaric acid, hydroxyglycine, a salt of the acid, and combinations of two or more thereof).

The titanium tetrahydrocarbyloxides suitable for use in the present invention can also be produced by, for example, mixing titanium tetrachloride and an alcohol in the presence of a base, such as ammonia, to form the tetraalkyl titanate. The alcohol typically is ethanol, n-propanol, isopropanol, n-butanol, or isobutanol. Methanol generally is not employed because the resulting tetramethyl titanate is insoluble in the reaction mixture, complicating its isolation. Tetraalkyl titanates thus produced can be recovered by first removing by-product ammonium chloride by any means known to one skilled in the art such as filtration followed by distilling the tetraalkyl titanate from the reaction mixture. This process can be carried out at a temperature in the range of from about 0 to about 150° C. Titanates having longer alkyl groups can also be produced by transesterification of those having R' groups up to $C_4$ with alcohols having more than 4 carbon atoms per molecule.

Examples of commercially available organic titanium compounds include, but are not limited to, TYZOR® TPT and TYZOR® TBT (tetra isopropyl titanate and tetra n-butyl titanate, respectively) available from E. I. du Pont de Nemours and Company, Wilmington, Del., U.S.A.

The presently preferred solubility promoter can be an organic silicate, organic zirconate, or combinations thereof. Presently, it is most preferred that a solubility promoter can facilitate the dissolution of essentially all of the titanium present in the catalyst composition in a solvent used to prepare the composition, at room temperature (about 25° C.), at catalyst composition concentrations that are desired for the particular application. Typically the components are selected to form a catalyst composition that is dissolved in concentrations of at least 3 grams, preferably at least 5 grams, of catalyst per 100 grams of solvent, to minimize the amount of solvent introduced to a process employing the catalyst. The presently most preferred solubility promoters include, but are not limited to, organic ortho silicates, organic ortho zirconates, or combinations thereof.

The organic ortho silicates have the formula of $Si(OR^1)_4$ and the organic ortho zirconates have the formula of $Zr(OR^1)_4$ in which each $R^1$ can be the same or different and is a hydrocarbyl radical having 1 to about 10, preferably 1 to about 8, and most preferably 1 to 5 carbon atoms per radical. The presently preferred $R^1$ is an alkyl radical, either branched or straight chain. These solubility promoters are generally commercially available or can be produced by, for example, introducing a silicon tetrachloride or zirconium tetrachloride into a solvent disclosed above to replace the chlorides with the $R^1$ groups in the solvent.

Examples of suitable solubility promoters include, but are not limited to, tetraethyl ortho silicate, tetra-n-propyl ortho silicate, tetra n-propyl ortho zirconate, tetra n-butyl ortho zirconate, and combinations of two or more thereof. Tetraethyl ortho silicate and tetra-n-propyl ortho silicate are commercially available. Tetra n-propyl ortho zirconate and tetra n-butyl ortho zirconate are organic zirconates commercially available from E. I. du Pont de Nemours and Company under the "TYZOR®" trademark.

It is presently preferred that the phosphorus source be selected from a phosphonic acid, a phosphinic acid, a phosphine, or combinations of two or more thereof. The phosphorus source can have an alkyl, alkenyl, alkaryl, aryalkyl, or aryl group directly bonded to the phosphorus atom. Typically each group can contain 1 to about 25, preferably 1 to about 20, and most preferably 1 to 15 carbon atoms per group. For example, methyl group, ethyl group, a phenyl group, or naphthyl group can be present. These groups can further be substituted with substituent groups that do not unduly interfere with the preparation of the catalyst composition or subsequent reactions employing the catalyst. Furthermore, the hydroxyl group of the acid can also be substituted. For example, one or two OH groups bonded to the phosphorus atom of a phosphonic acid can be esterified.

Examples of suitable phosphorus sources include, but are not limited to, phenyl phosphinic acid, diphenyl phosphinic acid, 3-(hydroxyphenylphosphinyl) propanoic acid, 1,2-bis-diphenylphosphinoethane, 1,3-bis-diphenylphosphinopropane, 1,4-bis-diphenylphosphinobutane, bis-4-tolylphosphine oxide, bis-3,5-xylylphosphine oxide, or combinations of two or more thereof.

Any solvent that can substantially dissolve the catalyst composition disclosed above can be used in the present invention. The presently preferred solvent is an alcohol having the formula of $R^1(OH)z_n$, an alkylene glycol of the formula $(HO)_n(ON)_n$, a polyalkylene glycol or alkoxylated alcohol having the formula of $R^1O[CH_2CH(R^1)O]_nH$, or combinations of two or more thereof in which each $R^1$ is the same as that disclosed above. A is an alkylene group and can have 2 to about 10, preferably 2 to about 7, and most preferably 2 to 4 carbon atoms per molecule. Each n can be the same or different and is independently a number in the range of from 1 about to about 10, preferably 1 to about 7, and most preferably 1 to 5. Examples of suitable solvents include, but are not limited to, ethanol, propanol, isopropanol, butanol, ethylene glycol, propylene glycol, isopropylene glycol, butylene glycol, 1-methyl propylene glycol, pentylene glycol, diethylene glycol, triethylene glycol, cyclohexyl-bis-1,4-dimethanol diethylene glycol monomethyl ether, triethylene glycol monomethylether, 2-ethyl hexanol, and combinations of two or more thereof.

The presently preferred solvent is ethylene glycol for the polyester produced therefrom has a wide range of industrial applications.

According to the invention, the catalyst composition can also comprise, consist essentially of, or consist of an organic titanium compound, a complexing agent, and a phosphorus source. The composition can also comprise, consist essentially of, or consist of an organic titanium compound, a complexing agent, a phosphorus source, and a solvent. The composition can also consist essentially or consist of an organic titanium compound, a complexing agent, a phosphorus source, a solvent, and a sulfonic acid. The titanium compound, phosphorus source, and solvent are the same as those disclosed above.

The complexing agents suitable for use in the present invention are generally hydroxycarboxylic acids, aminocarboxylic acids, or combinations of two or more thereof. It is presently preferred that the complexing agents be α-hydroxycarboxylic acids, hydroxyalkyl α-aminocarboxylic acids, or combinations thereof in which the alkyl group has 1 to about 15, preferably 1 to 10 carbon atoms per group, and combinations of two or more thereof. Examples of suitable complexing agents include, but are not limited to, lactic acid, glycolic acid, citric acid, tartaric acid, malic acid, glycine, bis-hydroxyethyl glycine, hydroxyethyl glycine, and combinations of two or more thereof.

The presently preferred sulfonic acids can be any aryl or alkyl sulfonic acids that can be substantially soluble in a solvent disclosed above. Examples of suitable sulfonic acids include, but are not limited to, p-toluene sulfonic acid, benzene sulfonic acid, methane sulfonic acid, ethane sulfonic acid, propane sulfonic acid, butane sulfonic acid, and combinations of two or more thereof. The salt of sulfonic acid can be an alkali metal salt, an alkaline earth metal salt, an ammonium salt, or combinations of two or more thereof.

The molar ratio of solubility promoter or complexing agent to titanium compound can be in the range of from about 0.1:1 to about 5:1, preferably about 0.5:1 to about 5:1, and most preferably 1:1 to 3:1. The molar ratio of phosphorus source to titanium compound, measured as P:Ti, can be in the range of from about 0.1:1 to about 10:1, preferably about 0.5:1 to about 5:1, and most preferably 1:1 to 3:1. The molar ratio of sulfonic acid, if present, to titanium compound ($SO_3$:Ti) is generally preferred to be about 0.0001:1 to less than or equal to 2:1, preferably less than or equal to 1:1, and most preferably less than or equal to 0.5:1. Alternatively, the titanium compound can be present in the catalyst composition in the range of from about 0.01 to about 15, preferably about 0.1 to about 10, and most preferably 0.5 to 5 percent (%), based on total weight of the composition as 100%.

The catalyst composition can be produced by any means known to one skilled in the art and, therefore, the disclosure of which is omitted herein for the interest of brevity.

Any glycol that can esterify an acid or transesterify an ester can be used in the formation of the bis-glycolate ester. The presently preferred glycol is an alkylene glycol having the formula of $(HO)_nA(OH)_n$ in which A and n are the same as disclosed above. Examples of suitable glycols include, but are not limited to, ethylene glycol, propylene glycol, isopropylene glycol, butylene glycol, 1-methyl propylene glycol, pentylene glycol, diethylene glycol, triethylene glycol, 1,6-hexanediol, cyclohexyl-1,4-bismethanol, and combinations of two or more thereof. The presently most preferred alcohol is an alkylene glycol such as ethylene glycol for the polyester produced therefrom has a wide range of industrial applications.

The molar ratio of the starting material, $(RO(O)C)_2ArS(O)_2OM$, to glycol can be any ratio so long as a desired bis-glycol ester of the invention can be produced. Generally, the ratio can be in the range of from about 0.1:1 to about 10:1, preferably about 0.2:1 to about 1:1.

According to the second embodiment of the invention, a process that can be used for producing a cationic dyeable polyalkylene terephthalate is provided. The process comprises contacting, (a) a mixture comprising (i) terephthalic acid or dialkyl terephthalate and (ii) the bis-glycolate ester of 5-sulfoisophthalate metal salts produced in the first embodiment of the invention, in the presence of an esterification or transesterification catalyst, with a glycol. The bis-glycolate esters of the 5-sulfo isophthalate metal salts are disclosed in the first embodiment of the invention and the glycol can be the same as that disclosed above.

According to the second embodiment of the present invention, the catalyst can be any esterification or transesterification catalyst such as antimony; a titanium compound; an organic titanate disclosed above; a composition comprising an organic titanate compound and an additional component selected from the group consisting of a solubility promoter, a phosphorus source, a sulfonic acid, and combinations of two or more thereof; a catalyst composition disclosed above in the first embodiment of the invention; and combinations of two or more thereof.

A preferred process for producing cationic dyeable polyester comprises, consists essentially of, or consists of contacting a mixture with a catalyst. The mixture can comprise, consist essentially of, or consist of a glycol, a terephthalic acid or dialkyl terephthalate, and a bis-glycolate ester of 5-sulfo isophthalate metal salt produced by the process disclosed in the first embodiment of the invention.

The contacting of the mixture with a catalyst can be carried out by any suitable means. For example, the individual compositions of the mixture can be combined before being contacted with the catalyst. However, it is presently preferred that the catalyst be first dissolved or dispersed in a glycol by any suitable means such as mechanical mixing or stirring to produce a solution or dispersion followed by combining the solution or dispersion with (1) a mixture of TPA or dialkyl terephthalate and a bis-glycolate of 5-sulfo isophthalate metal salt and (2) a glycol under an effective esterification or transesterification condition sufficient to effect the production of a cationic dyeable polyalkylene terephthalate.

A suitable condition to effect the production of a cationic dyeable polyalkylene terephthalate can include a temperature in the range of from about 60° C. to about 350° C., preferably about 150° C. to about 300° C., and most preferably 250–300° C. under a pressure in the range of from about 0.001 to about 10 atmospheres for a time period of from about 0.1 to about 20, preferably about 0.2 to about 15, and most preferably 0.5 to 10 hours.

The molar ratio of glycol to terephthalic acid or dialkyl terephthalate can be any ratio so long as the ratio can effect the production of cationic dyeable polyester. Generally the ratio can be in the range of from about 1:1 to about 10:1, preferably about 1:1 to about 5:1, and most preferably about 1:1 to about 3:1. The concentration of the bis-glycolate ester of 5-sulfo isophthalate metal salt in the mixture is such that the cationic dyeable polyester contains about 0.5 to about 10, preferably about 1 to 7, and most preferably about 2 to about 5 weight % of this monomer. Generally, a bis-glycolate ester of 5-sulfo isophthalate metal salt can be present in the mixture in the range of at least from about 0.1 to about 10, preferably about 1 to about 7, and most preferably 2 to 5 weight %, based on the weight of the mixture.

The catalyst can be present in an amount corresponding to about 1 to about 1,000, preferably about 10 to about 500, and most preferably about 100 to about 300 ppm by weight of titanium relative to the weight of the bis-glycolate ester. However, the optimum amount of catalyst may vary with the particular catalyst composition chosen or the polymer characteristics desired. The primary changes to be expected are a shorter reaction time and improved color of the cationic dyeable polyester product.

While the individual components in the above reaction can be combined in any order, it is generally preferred that, for maximum efficiency, the catalyst be added last, preferably before a desired temperature of the mixture is reached.

The invention is illustrated, but not limited, by the following examples. All TYZOR® products noted in the examples were obtained from DuPont, Wilmington, Del., USA.

Typically, the bis-glycolate ester of 5-sulfo isophthalate metal salt is commercially produced by transesterification of the corresponding dimethyl ester, which is readily available by purchase from E. I. duPont de Nemours & Co., Wilmington, Del. Typically, dimethyl 5-sulfo isophthalate metal salt is added to an excess of ethylene glycol, along with a small amount of buffering agent and catalyst, and agitated under an inert atmosphere. The catalyst is typically manganese acetate or an organic titanate such as tetraisopropyl titanate and the buffering agent is typically sodium acetate. The temperature is then raised over a period of several hours to remove the by-product methanol and drive the reaction to completion, typically to a temperature between 125° C. and 185° C. The chosen temperature and reaction time determine the final product composition as the 9 various possible esters of the 5-sulfo isophthalate metal salt. For example, in a typical run at 145° C. and 2 hours reaction time using manganese acetate catalyst, the percentage of the di-glycol monomer was 56.9%, the di-glycol dimer was 6.0%, the glycol-methanol monomer was 31.5%, and the di-methanol monomer was 4.9%.

When the bis-glycolate ester of 5-sulfo isophthalate metal salt is prepared instead by esterification of 5-sulfo isophthalic acid metal salt, the basic procedure is similar. In general, 5-sulfo isophthalate metal salt is added to an excess of ethylene glycol, along with a small amount of buffering agent and catalyst, and agitated under an inert atmosphere. The catalyst is typically tetraisopropyl titanate; the buffering agent is typically sodium acetate. This process is also well known and can be readily carried out by one skilled in the art. However, care must be taken to add the 5-sulfo isophthalic acid metal salt to the ethylene glycol in portions, slowly and with good agitation at 60–90C., because of a tendency for the undissolved salt to agglomerate into a solid mass. The temperature is raised to drive the reaction to completion. As before, the preferred temperature range is from 125° C. to 185° C.

As shown in the examples below, using the invention process, a shorter reaction time and/or improved color of the cationic dyeable polyester product can be obtained.

Color of the resulting cationic dyeable polyester polymer was measured in terms of the L-value and b-value, using an instrument such as the SP-78 Spectrophotometer. The L-value shows brightness, with the greater the numerical value showing higher (desirable) brightness. Preferably, the L-value will be equal to or higher than that of polymer using the prior art catalysts. The b-value shows the degree of yellowness, with a higher numerical value showing a higher (undesirable) degree of yellowness. Preferably, the b-value will be equal to or lower than that of the polymer made using the prior art catalysts. Because the color measurement is well known to one skilled in the art, its description is omitted herein for the interest of brevity.

Preparation of the Catalyst

Example-1A

A 500 ml flask was charged with 109.4 g of ethylene glycol. Agitation was started and 100 g of phenylphosphinic acid was added. The reaction mass was heated to 60° C. and held at 60° C. until all the solids dissolved. Then 36.9 g of tetraethyl orthosilicate followed by 50 g of tetraisopropyltitanate were added dropwise. The reaction mass was held 1 hr. at 50–60° C. and then cooled and bottled to give 369.4 g of a pale yellow solution containing 2.3% Ti.

Example-1B

A 5 liter flask was charged with 3560 g of ethylene glycol. Agitation was started and 209.4 g of phenylphosphinic acid was added. The reaction mass was heated to 60° C. and held there until all the solids dissolved. Then 98.8 g of malic acid, 141.6 g of anhydrous citric acid and 70.8 g of p-toluenesulfonic acid monohydrate was added. The reaction mass was held at 60° C. until all the solids dissolved and then 418.8 g of tetraisopropyl titanate was added dropwise over 30 minutes. The reaction mass was held at 60° C. an additional hour and then cooled to give 4500 g of a pale yellow solution containing 1.57% Ti.

Preparation of the Bis-glycolate Ester from NaSIPA (Comparative) Example-2

An ethylene glycol solution of the bis-glycolate ester was produced by slowly adding 91 g (0.338 moles) of 5-sulfo isophthalate sodium salt to 266.7 g (4.30 moles) of ethylene glycol at 60° C. while stirring in a clean nitrogen-purged vessel equipped with a mechanical agitator and a condenser. Then 0.28 g (0.0034 moles) of anhydrous sodium acetate was added as buffer, followed by 0.12 g (0.00042 moles) of tetraisopropyl titanate (TYZOR®TPT) as catalyst. The vessel was then heated to 180° C. over a period of 1.5 to 2.0 hours, using a subsurface purge with nitrogen at all times to facilitate removal of water and insure process safety. The reaction was continued for 4 hours, and then cooled to room temperature to give 304.7 g of a clear 39.7% solution of the bis-glycolate ester.

Example-3

Example-2 was repeated using 1 g (0.00048 moles) of catalyst prepared in Example 1A to give 318.9 g of a clear 36.1% solution.

Example-4

Example-2 was repeated using 1.28 g (0.00042 moles) of catalyst prepared in Example-1B to give 339.2 g of a clear 36.9% solution.

The table below shows the composition of the resulting product after 4 hours at 180 C. The abbreviations are as follows: % EG-EG is the percent of bis-glycolateate ester; % EG-EG dimer is the percent of bis-glycolate dimer; % EG-OH is the percent of hydroxyl ethylene mono glycolate ester; and % EG-DEG is the percent of the ethylene glycol-diethylene glycol mixed ester.

TABLE 1

Bis-glycolate Ester from NaSIPA (4 Hr. @ 180 C.)

| | % EG-EG | % EG-EG dimer | % EG-OH | % EG-DEG |
|---|---|---|---|---|
| (Comp.) Example 2 | 78.17 | 13.77 | 0.80 | 7.07 |
| Example 3 | 81.37 | 11.25 | 0.70 | 4.99 |
| Example 4 | 83.57 | 10.84 | 1.03 | 4.02 |

This table shows that the inventive catalyst compositions (Examples 3 and 4) produced a glycolate ester composition with a slightly higher amount of the desired bis-glycolate ester product (the % EG-EG) than the comparative Example 2.

Preparation of the Bis-glycolate Ester from NaDMSIP (Comparative) Example-5

An ethylene glycol solution of the bis-glycolate ester was produced by slowly adding 100 g (0.372 moles) of 5-sulfo dimethyl isophthalate sodium salt to 222 g (43.58 moles) of ethylene glycol at 80° C. while stirring in a clean nitrogen-purged vessel equipped with a mechanical agitator and a condenser. Then 0.28 g (0.0034 moles) of anhydrous sodium acetate was added as buffer, followed by 0.12 g (0.00042 moles) of tetraisopropyl titanate (TYZOR®TPT) as catalyst. The vessel was then heated to 180° C. over a period of 1.5 to 2.0 hours, using a subsurface purge with nitrogen at all times to facilitate removal of methanol and insure process safety. The reaction was continued for 4 hours, and then cooled to room temperature to give 260 g of a clear solution of the bis-glycolate ester.

Example-6

Example-5 was repeated using 1 g ( 0.00048 moles) of the catalyst prepared in Example 1-A to give 267.9 g of a clear 49.6% solution.

Example-7

Example-5 was repeated using 1.4 g (0.00046 moles) of the catalyst prepared in Example 1-B to give 272.5 g of a clear 42% solution.

The table below shows the composition of the resulting products after 4 hours at 180 C. The abbreviations are as in the previous table.

TABLE 2

Bis-glycolate Ester from NaDMSIP (4 Hr. @ 180 C.))

| | % EG-EG | % EG-EG dimer | % EG-OH | % EG-DEG |
|---|---|---|---|---|
| (Comp.) Example 5 | 85.94 | 12.72 | 0.65 | 0.53 |
| Example 6 | 84.34 | 13.90 | 1.33 | 0.42 |
| Example 7 | 83.61 | 12.88 | 1.49 | 0.91 |

This table shows that, for NaDMSIP, the inventive catalyst compositions (Examples 6 and 7) produced a glycolate ester composition with a slightly lower amount of the desired bis-glycolate ester product (the % EG-EG) than the comparative Example 5. In this case, the advantage of the inventive composition showed up primarily when the bis-glycolate ester was used to make the Sulfo-modified PET (Table 4).

Example 8. Preparation of the PET Olizomer from DMT

The DMT-based oligomers used in these examples were made from dimethyl terephthalate, ethylene glycol, with no added antimony catalyst. They were prepared as follows:

An autoclave was charged with 100 lbs. (45.4 Kg) of dimethyl terephthalate, 67 lbs. (30.4 Kg) of ethylene glycol and 4.4 g of zinc acetate dihydrate. The batch was heated to 240 C. at an agitation speed of 15 rpm, and 33 lbs. (15.0 Kg) of methanol and 14.3 lbs (6.5 Kg) of ethylene glycol removed. The charge was then heated to 275 C. over the course of 90 minutes, and the remaining ethylene glycol removed at 285 C. and below 2 mm Hg vacuum. Once the condensation mass was judged to be complete, the molten mass was extruded into an aqueous bath to solidify the product. The resultant polymer was dried to remove residual moisture before use.

Example 9 Preparation of the Sulfo-modified PET

A 1 liter autoclave was charged with 489 g of DMT-based oligomer prepared as in Example 10, 33 g of a 35% active ingredient solution of bis-glycolate ester of 5-sulfo isophthalate sodium salt in ethylene glycol, and 138 g of ethylene glycol. This corresponds to a total loading of 500 g of DMT based oligomer and 160 g of ethylene glycol. This calculates to a 2% loading of the SIPA on the weight of the PET polymer. Then 0.18 g of antimony oxide catalyst was added. Agitation and heating were started and the charge heated to 270–280° C. while removing volatiles under atmospheric pressure. When the melt reached 270° C., a vacuum was applied. When the charge reached 280–285° C., the vacuum was reduced to 2–2.5 mm Hg. Heating was continued at 280–285 C. and 2–2.5 mm Hg until a torque reading of 15 was obtained. The charge was drowned in water and oven aged at 160° C. overnight. Inherent viscosity (IV) and color were reported for each sample. Finishing time was measured from the time the vacuum reached 2–2.5 mm Hg until the torque reached 15 oz-in (ounce-inches) as measured by an Electro-Craft Monomatic torque controller.

The color of the resulting polymer was measured in terms of the L-value and b-value, using the SP-78 Spectrophotometer. Examples 10 and 11 below were each carried out using the bis-glycolate ester made in comparative Example 2, while Example 12 was carried out using the bis-glycolate ester made in inventive Example 3. The results are shown in Table 3.

TABLE 3

Reaction Time and Color for NaSIPA Examples

| Examples | Time (min) | L Color | b Color | Notes |
|---|---|---|---|---|
| Comparison Run | 100 | 75.20 | 6.23 | a |
| Example 10 | 90 | 72.56 | 7.51 | b |
| Example 11 | 40 | 77.47 | 6.88 | c |
| Example 12 | 35 | 79.21 | 6.35 | d |

Notes:
a. This was comparison run with no bis-glycolate ester added, using 300 ppm antimony as the polycondensation catalyst.
b. This was a run with 2% bis-glycolate ester made in comparative Example 2, using no polycondensation catalyst
c. This was a run with 2% bis-glycolate ester made in comparative Example 2, using 300 ppm antimony as polycondensation catalyst.
d. This was a run with 2% bis-glycolate ester made in inventive Example 3, using 300 ppm antimony as polycondensation catalyst.

The above table shows that bis-glycolate ester of NaSIPA made with the invention catalyst produced cationic dyeable polyester having improved L and/or b color performance over cationic dyeable polyester produced using tetraisopropyl titanate (TYZOR®TPT) catalyst.

The following table shows the results when using bis-glycolate ester made from NaDMSIP. Example 13 below was carried out using a bis-glycolate ester made using a manganese acetate transesterification catalyst, while Examples 14 and 15 were carried out using the bis-glycolate ester made in inventive Examples 6 and 7, respectively. The results are shown in Table 4.

TABLE 4

Reaction Time and Color for NaDMSIP Examples

| Examples | Time (min) | L Color | b Color | Notes |
|---|---|---|---|---|
| Example 13 | 60 | 73.08 | 9.7 | a |
| Example 14 | 65 | 73.36 | 9.41 | b |
| Example 15 | 45 | 75.63 | 6.26 | c |

Notes:
a. This was a comparative example using commercially available 2% bis-glycolate ester from NaDMSIP and manganese acetate transeterification catalyst, using 300 ppm antimony as polycondensation catalyst
b. This was a run with 2% bis-glycolate ester made in example 6, using 300 ppm antimony as polycondensation catalyst
c. This was a run with 2% bis-glycolate ester made in example 7, using 300 ppm antimony as polycondensation catalyst The above table shows that bis-glycolate ester of NaDM-SIP made with novel titanate catalysts produced cationic dyeable polyester with improved L and/or b color performance over cationic dyeable polyester made using manganese acetate catalysts.

That which is claimed is:

1. A process comprising contacting a 5-sulfo isophthalic acid metal salt or a dialkyl ester of a 5-sulfo isophthalate metal salt, in the presence of a catalyst, with a glycol wherein said catalyst is selected from the group consisting of (1) a catalyst which comprises a titanium compound, a solubility promoter, and a phosphorus source, (2) a catalyst which comprises a titanium compound, a complexing agent, and a phosphorus source, and (3) combinations thereof; said solubility promoter is selected from the group consisting of ortho silicates, ortho zirconates, and combinations thereof; and said complexing agent is selected from the group consisting of hydroxycarboxylic acids, aminocarboxylic acids, and combinations thereof.

2. A process according to claim 1 wherein said catalyst comprises a titanium compound, a solubility promoter, and a phosphorus source; said solubility promoter is selected from the group consisting of ortho silicates, ortho zirconates and combinations thereof; and said phosphorus source is selected from the group consisting of a phosphonic acid, a phosphinic acid, a phosphine, and combinations of two or more thereof.

3. A process according to claim 1 wherein said catalyst comprises a titanium compound, a complexing agent, and a phosphorus source; said complexing agent is selected from the group consisting of hydroxycarboxylic acids, aminocarboxylic acids, and combinations thereof; and said phosphorus source is selected from the group consisting of a phosphonic acid, a phosphinic acid, a phosphine, and combinations of two or more thereof.

4. A process according to claim 3 wherein said catalyst further comprises a sulfonic acid.

5. A process according to any of claims 1 to 4 wherein said titanium compound has the formula of formula $Ti(OR')_4$ wherein each R' is independently selected from the group consisting of an alkyl radical, a cycloalkyl radical, an aralkyl hydrocarbon radical, and combinations of two or more thereof.

6. A process according to claim 5 wherein said titanium is selected from the group consisting of titanium tetraethoxide, titanium tetrapropoxide, titanium tetraisopropoxide, titanium tetra-n-butoxide, titanium tetrahexoxide, titanium tetra 2-ethylhexoxide, titanium tetraoctoxide, and combinations of any two or more thereof.

7. A process according to any of claims 1 to 4 or claim 6 wherein said catalyst further comprises a solvent.

8. A process according to claim 7 wherein said solvent is an alcohol.

9. A process according to claim 2, 5, 6, or 8 wherein said solubility promoter is selected from the group consisting of $Si(OR^1)_4$, $Zr(OR^1)_4$, and combinations thereof; each R' is independently a hydrocarbyl radical having 1 to about 10 carbon atoms per radical.

10. A process according to claim 9 wherein said solubility promoter is selected from the group consisting of tetraethyl ortho silicate, tetra-n-propyl ortho silicate, tetra n-propyl ortho zirconate, tetra n-butyl ortho zirconate, and combinations of two or more thereof.

11. A process according to claim 4, 5, 6, or 8 wherein said complexing agent is selected from the group consisting of hydroxycarboxylic acids, aminocarboxylic acids, and combinations thereof.

12. A process according to claim 11 wherein said complexing agent is selected from the group consisting of α-hydroxycarboxylic acids, hydroxyalkyl α-aminocarboxylic acids, and combinations thereof.

13. A process according to claim 12 wherein said complexing agent is selected from the group consisting of lactic acid, glycolic acid, citric acid, tartaric acid, malic acid, glycine, bis-hydroxyethyl glycine, hydroxyethyl glycine, and combinations of two or more thereof.

14. A process according to any of claims 1 to 13 wherein said 5-sulfo isophthalic acid metal salt or a dialkyl ester of a 5-sulfo isophthalate metal salt has the formula of $(RO(O)C)_2ArS(O)_2OM$; each R is independently selected from the group consisting of hydrogen, an alkyl group, and combinations thereof; Ar is a phenylene group; and M is an alkali metal ion.

15. A process according to claim 14 wherein at least one R is hydrogen.

16. A process according to claim 14 wherein at least one R is methyl group.

17. A process according to claim 15 or 16 wherein M is sodium ion.

18. A process comprising contacting a mixture, in the presence of a catalyst, with a glycol under a condition effective to produce a polyester wherein said mixture comprises (i) terephthalic acid or dialkyl terephthalate and (ii) the bis-glycolate ester of 5-sulfoisophthalate metal salts produced by the process recited in any of claims 1 to 17.

19. A process according to claim 18 wherein said catalyst is selected from the group consisting of antimony compound; titanium compound; organic titanate; a catalyst recited in any of claims 1 to 17; and combinations of two or more thereof.

20. A process according to claim 19 wherein said bis-glycolate esters of 5-sulfo isophthalate metal salt is present in said polyester in the range of from about 1 to about 7 weight % of said polyester.

21. A process according to claim 19 wherein said bis-glycolate esters of 5-sulfo isophthalate metal salt is present in said polyester in the range of from about 2 to about 5 weight % of said polyester.

* * * * *